United States Patent
An et al.

(10) Patent No.: US 11,235,157 B2
(45) Date of Patent: Feb. 1, 2022

(54) HEART RATE INDICATED ATRIOVENTRICULAR DELAY OPTIMIZATION

(71) Applicant: Cardiac Pacemakers, Inc., St. Paul, MN (US)

(72) Inventors: Qi An, Blaine, MN (US); Yinghong Yu, Shoreview, MN (US); Adam MacEwen, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 238 days.

(21) Appl. No.: 16/694,229

(22) Filed: Nov. 25, 2019

(65) Prior Publication Data

US 2020/0188677 A1 Jun. 18, 2020

Related U.S. Application Data

(60) Provisional application No. 62/779,792, filed on Dec. 14, 2018.

(51) Int. Cl.
*A61N 1/365* (2006.01)
*A61N 1/362* (2006.01)
*A61N 1/368* (2006.01)

(52) U.S. Cl.
CPC ....... *A61N 1/36592* (2013.01); *A61N 1/3627* (2013.01); *A61N 1/3682* (2013.01); *A61N 1/36843* (2017.08)

(58) Field of Classification Search
None
See application file for complete search history.

(56) References Cited

U.S. PATENT DOCUMENTS

2016/0051823 A1 2/2016 Maile et al.
2018/0361162 A1 12/2018 Ternes et al.

*Primary Examiner* — Jon Eric C Morales
(74) *Attorney, Agent, or Firm* — Schwegman Lundberg & Woessner, P.A.

(57) ABSTRACT

Systems and methods for monitoring and treating patients with heart failure are discussed. The system can store in a memory stimulation parameters, including stimulation timing parameters for a plurality of heart rate ranges. The system includes a plurality of timers with respective durations for the plurality of heart rate ranges. A stimulation control circuit can identify a target heart range in which a detected heart rate falls, and measure an atrioventricular (AV) conduction characteristic value in response to the timer for the target heart range being expired at the detected heart rate. The stimulation control circuit can update a stimulation parameter corresponding to the target heart rate range using the measured AV conduction characteristic. The updated stimulation parameter can be used in cardiac stimulation.

20 Claims, 7 Drawing Sheets

FIG. 5A

| HR (bpm) | AS | AP |
|---|---|---|
| <60 | -- | -- |
| 60-70 | -- | -- |
| 70-80 | -- | -- |
| 80-90 | -- | -- |
| 90-100 | -- | -- |
| >100 | -- | -- |

| HR (BPM) | SUPINE | | SITTING | | STANDING | |
|---|---|---|---|---|---|---|
| | AS | AP | AS | AP | AS | AP |
| <60 | -- | -- | -- | -- | -- | -- |
| 60-70 | -- | -- | -- | -- | -- | -- |
| 70-80 | -- | -- | -- | -- | -- | -- |
| 80-90 | -- | -- | -- | -- | -- | -- |
| 90-100 | -- | -- | -- | -- | -- | -- |
| >100 | -- | -- | -- | -- | -- | -- |

| HR (bpm) | DAYTIME | | NIGHTTIME | |
|---|---|---|---|---|
| | AS | AP | AS | AP |
| <60 | -- | -- | -- | -- |
| 60-70 | -- | -- | -- | -- |
| 70-80 | -- | -- | -- | -- |
| 80-90 | -- | -- | -- | -- |
| 90-100 | -- | -- | -- | -- |
| >100 | -- | -- | -- | -- |

530

HEART RATE INDICATED ATRIOVENTRICULAR DELAY OPTIMIZATION

CLAIM OF PRIORITY

This application claims the benefit of priority under 35 U.S.C. § 119(e) of U.S. Provisional Patent Application Ser. No. 62/779,792, filed on Dec. 14, 2018, which is herein incorporated by reference in its entirety.

TECHNICAL FIELD

This document relates generally to medical systems and devices, and more particularly, to systems, devices, and methods of electrostimulation for treating heart failure.

BACKGROUND

Congestive heart failure (CHF) is a leading cause of death in the United States and globally. CHF occurs when the heart is unable to adequately supply enough blood to maintain a healthy physiological state. CHF may be treated by drug therapy, or by electrostimulation therapy.

Implantable medical devices (IMDs) have been used to monitor CHF patients and manage heart failure in an ambulatory setting. Some IMDs may include sensors to sense physiological signals from a patient, and detect worsening heart failure, such as heart failure decompensation. Frequent patient monitoring and early detection of worsening heart failure may help improve patient outcome. Identification of patient at an elevated risk of future heart failure events may help provide timely treatment and prevent or reduce hospitalization. Identifying and safely managing the patients at risk of worsening heart failure can avoid unnecessary medical interventions, hospitalization, and reduce healthcare cost.

An IMD may include a pulse generator and electrical circuitry configured to electrically stimulate a heart or other excitable tissue, to help restore or improve the cardiac performance, or to correct cardiac arrhythmias. One example of the electrostimulation therapy is cardiac resynchronization therapy (CRT). CRT, typically delivered as biventricular (BiV) pacing or synchronized left ventricle (LV)-only pacing, may be indicated for CHF patients with moderate to severe symptoms and ventricular dyssynchrony. CRT keeps the LV and right ventricle (RV) pumping synchronously by sending electrical stimuli to both the LV and RV. The synchronized stimulation may improve heart pumping efficiency and increase blood flow in some CHF patients. CRT can decrease hospitalization and morbidity associated with worsening heart failure, as well as improvements in quality of life.

SUMMARY

This document discusses, among other things, a patient management system for monitoring and treating patients with heart failure. The system may store in a memory a set of stimulation parameters, including stimulation timing parameters for a plurality of heart rate ranges. The system may include respective timers for the plurality of heart rate ranges. A stimulation control circuit can program the timers with respective durations, identify from the plurality of heart rate ranges a target heart range in which a detected heart rate falls, and measure an atrioventricular (AV) conduction characteristic value in response to the timer for the target heart range being expired at the detected heart rate. The stimulation control circuit can update a stimulation parameter, corresponding to the target heart rate range, using the measured AV conduction characteristics. The updated stimulation parameter can be used for cardiac pacing.

Example 1 is a medical-device system, comprising a stimulation control circuit configured to generate a control signal to deliver cardiac stimulation to a heart of a patient according to stimulation parameters stored in a memory according to a plurality of heart rate ranges, and to update at least a portion of the stored stimulation parameters. The update of a portion of the stimulation parameters include: provide a plurality of timers each having a duration, wherein each of the plurality of timers corresponds to different heart rate ranges, and is configured to expire after the respective duration has elapsed from a respective reset time; identify, from the plurality of heart rate ranges, a target heart range in which a detected heart rate falls, and measure an atrioventricular conduction characteristic value if the timer for the target heart range has expired at the detected heart rate; and update at least a portion of the stimulation parameters stored in the memory and corresponding to the target heart rate range using the measured atrioventricular conduction characteristic.

In Example 2, the subject matter of Example 1 optionally includes the stimulation control circuit that can be configured to reset the timer for the target heart rate range upon measuring the atrioventricular conduction characteristic value.

In Example 3, the subject matter of any one or more of Examples 1-2 optionally includes the stimulation control circuit that can be configured to select a stimulation parameter value from the set of the stimulation parameters for a detected heart rate. The system can comprise a stimulator circuit configured to deliver cardiac stimulation using the selected stimulation parameter value.

In Example 4, the subject matter of any one or more of Examples 1-3 optionally includes the stimulation timing parameters that can include atrioventricular delay (AVD) values.

In Example 5, the subject matter of any one or more of Examples 1-4 optionally includes the atrioventricular conduction characteristic that can include intrinsic atrioventricular interval (AVI), and the stimulation control circuit can be configured to generate a control signal to suspend ventricular stimulation during the measurement of intrinsic AVI and to resume ventricular stimulation after the measurement of intrinsic AVI.

In Example 6, the subject matter of any one or more of Examples 1-5 optionally includes the stimulation control circuit that can be configured to generate, in response to the measurement of an atrioventricular conduction characteristic, a control signal to disable any subsequent measurement of atrioventricular conduction characteristic during a blanking period.

In Example 7, the subject matter of any one or more of Examples 1-6 optionally includes the stimulation control circuit that can be configured to determine a stimulation parameter for the target heart rate range using the measured atrioventricular conduction characteristic scaled a weight factor.

In Example 8, the subject matter of Example 7 optionally includes the stimulation control circuit that can be configured to update a stimulation parameter for the target heart rate range using a weighted combination of a historical stimulation timing parameter value and the measured atrioventricular conduction characteristic each scaled by respective weight factors.

In Example 9, the subject matter of any one or more of Examples 1-8 optionally includes a global timer having a duration, and the stimulation control circuit is configured to update at least the portion of the stimulation parameters in response to an expiration of the global timer.

In Example 10, the subject matter of any one or more of Examples 1-9 optionally includes the plurality of timers that can include a first timer for a first heart rate range, and a second timer for a second heart rate range higher than the first heart rate range. The stimulation control circuit can be configured to program the second timer with a duration shorter than a duration of the first timer.

In Example 11, the subject matter of any one or more of Examples 1-10 optionally includes the stimulation control circuit that can be configured to determine or update the respective durations of the plurality of timers using information of prevalence of heart rates detected in the corresponding plurality of heart rate ranges.

In Example 12, the subject matter of any one or more of Examples 1-11 optionally includes the stimulation control circuit that can be configured to store in the memory a stimulation parameter table including the set of stimulation timing parameters and the corresponding plurality of heart rate ranges.

In Example 13, the subject matter of any one or more of Examples 1-12 optionally includes the stimulation control circuit that can be configured to: generate, and store in the memory, a regression model between (1) values of the atrioventricular conduction characteristic corresponding to a plurality of heart rate ranges and (2) the plurality of heart rate ranges; and estimate a value of the atrioventricular conduction characteristic at a specific heart rate using the generated regression model.

In Example 14, the subject matter of any one or more of Examples 1-13 optionally includes the stored set of stimulation parameters that can further correspond to atrial sensed (AS) events or atrial paced (AP) events at the plurality of heart rate ranges, and the stimulation control circuit is configured to select the parameter for use during cardiac stimulation using information of a AS or AP event.

In Example 15, the subject matter of any one or more of Examples 1-14 optionally includes the stored set of stimulation parameters that can further include information of a pacing chamber configuration for a plurality of heart rate or heart rate ranges, the pacing chamber configuration including a left-ventricular (LV) only pacing or a bi-ventricular (BiV) pacing of both left and right ventricles, wherein the stimulation control circuit is configured to select the LV-only pacing or the BiV pacing using an atrioventricular interval or an atrioventricular interval variability at a sensed heart rate.

Example 16 is a method of operating a medical-device system to control cardiac stimulation using a plurality of timers corresponding to a plurality of heart rate ranges, each of the plurality of timers configured to expire after a respectively programmed duration has elapsed from a respective reset time. The method comprises steps of: monitoring patient heart rates; identifying, from the plurality of heart rate ranges, a target heart range in which a detected heart rate falls; measuring an atrioventricular conduction characteristic value if a timer for the target heart range has expired at the detected heart rate; and updating at least a portion of a set stimulation parameters stored in a memory and corresponding to the target heart rate range using the measured atrioventricular conduction characteristic; wherein the set of stimulation parameters include stimulation timing parameters corresponding to the plurality of heart rate ranges.

In Example 17, the subject matter of Example 16 optionally includes storing the set of stimulation parameters that can include storing in the memory a stimulation parameter table that includes the stimulation timing parameters for atrial sensed (AS) events or atrial paced (AP) events and corresponding to the plurality heart rate ranges.

In Example 18, the subject matter of any one or more of Examples 16-17 optionally includes thee stimulation timing parameters that can include atrioventricular delay (AVD) values. The atrioventricular conduction characteristic can include intrinsic atrioventricular interval (AVI). The method further comprises steps of generating a control signal to suspend ventricular stimulation during the measurement of intrinsic AVI, and after the measurement of intrinsic AVI, resuming ventricular stimulation and resetting the timer for the target heart rate range.

In Example 19, the subject matter of any one or more of Examples 16-18 optionally includes, subsequent to the measurement of intrinsic AVI, generating a control signal to disable any subsequent measurement of intrinsic AVI during a blanking period.

In Example 20, the subject matter of any one or more of Examples 16-19 optionally includes determining or updating the respective durations for the plurality of timers using information of prevalence of heart rates detected in the corresponding plurality of heart rate ranges.

In Example 21, the subject matter of any one or more of Examples 16-20 optionally includes updating at least a portion of the stimulation parameters includes using a weighted combination of a historical stimulation timing parameter value and the measured atrioventricular conduction characteristic each scaled by respective weight factors.

In Example 22, the subject matter of any one or more of Examples 16-21 optionally includes selecting a stimulation parameter value from the set of the stimulation parameters for a detected heart rate, and delivering cardiac stimulation via a stimulator circuit using the selected stimulation parameter value.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 5A-5C are diagrams illustrating patient condition-indicated stimulation parameter table stored in a memory that can be used for dynamic cardiac pacing.

DETAILED DESCRIPTION

Figure 1:
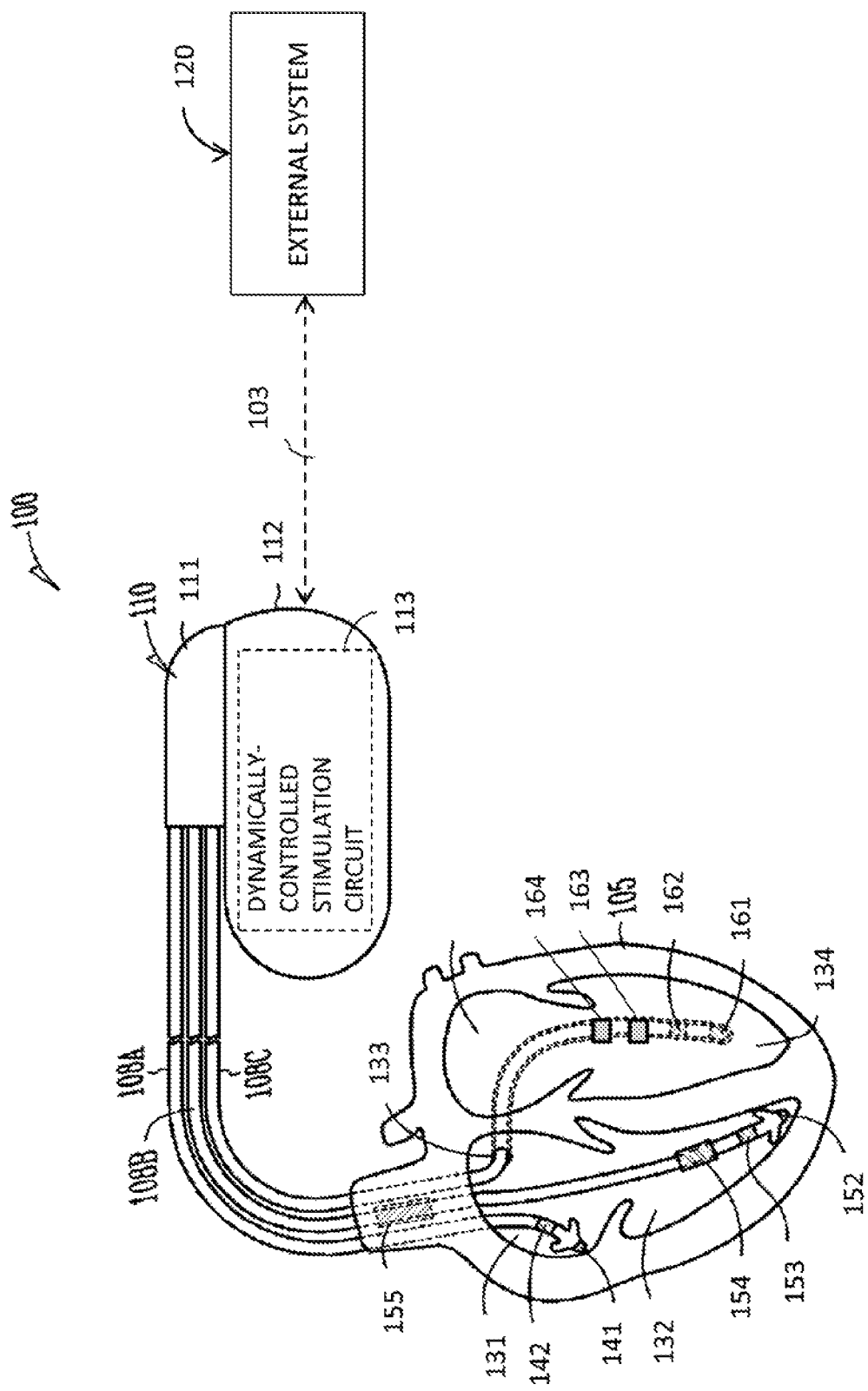
FIG. 1 illustrates an example of a patient management system and portions of an environment in which the system may operate.

Ambulatory medical devices (AMDs), such as IMDs, subcutaneous medical devices, wearable medical devices, or other external medical devices, may be used to detect worsening heart failure and deliver heart failure (HF) therapy to restore or improve the cardiac function. An IMD may be coupled to implanted leads with electrodes that may be used to sense cardiac activity, or to deliver HF therapy, such as cardiac stimulation. An AMD may have functionality of programmable therapy that allows for manual or automatic adjustment of electrostimulation parameters, such as stimulation chamber or site, stimulation mode, or stimulation timing.

An AMD can be configured to stimulation various cardiac chambers to restore cardiac synchrony and improve hemodynamics. During CRT or BiV pacing, synchronized stimulation may be applied to the LV and the RV of a heart. The RV and LV pacing sites may be stimulated concurrently, or sequentially with an RV-LV interventricular pacing delay (VVD). Delivery of LV and RV pacing may be timed relative to a fiducial point, such as an intrinsic atrial depolarization sensed by an atrial electrode (atrial sense, or AS), or an atrial pacing pulse (AP) that elicits atrial activation. If no intrinsic ventricular depolarization is detected within a period of atrial-ventricular delay (AVD) following the AS or the AP, the LV and RV pacing may be delivered at the end of the AVD.

In addition to BiV pacing, stimulation may be delivered only at one heart chamber, such as the LV. The LV-only pacing may improve cardiac synchrony in certain patients, such as those with intact AV conduction requiring cardiac resynchronization. Compared to the BiV pacing, LV-only pacing may require a simpler implantable procedure, consumes less power, and provides increased battery longevity. As such, it is clinically a valid alternative to more complicated BiV therapy regime. Similar to timing of BiV pacing, the LV pacing may be delivered at the end of a programmed AVD subsequent to the AS or the AP if no intrinsic LV depolarization is detected within the period of AVD.

An AMD can be configured to stimulate one or more sites of a heart chamber simultaneously or sequentially. In conventional single site pacing (SSP), only one site of a particular heart chamber (e.g., the LV) is stimulated. Alternatively, multisite pacing (MSP) can be used to as an alternative to SSP. The MSP involves electrostimulation at two or more sites in a heart chamber within a cardiac cycle. For example, in LV MSP, multiple LV sites may be simultaneously stimulated, or separated by one or more intra-LV time offset (ILVD). MSP may improve LV function and hemodynamic responses in some patients. However, MSP may require more energy than SSP, and may also increase the complexity of system design and operation. Not all CHF patients can uniformly benefit more from MSP than SSP.

A stimulation timing parameter, such as AVD, VVD, or ILVD discussed above, defines a timing sequence of cardiac stimulation. Because such timing sequence may affect therapy efficacy and patient hemodynamic outcome, proper selection or programming of a timing parameter can be important in HF management. For example, AVD can be determined using information about patient intrinsic AV conduction characteristics, such as an intrinsic AV interval (AVI) between a P wave and an R wave within a cardiac cycle in an electrocardiograph (ECG), or between an atrial sensed (AS) or atrial paced (AP) event to a ventricular sensed event (VS) within a cardiac cycle in an subcutaneously measured electrogram (EGM). In a patient, the intrinsic AVI may not stay constant, but vary under a multitude of physiological or functional conditions. For example, long-term changes in patient health conditions, HF progressions such as remodeling or decompensation, or short-term changes in heart rate, postures, posture transitions, physical activities, sleep/awake status, medication, hydration, diet, among other factors, may affect the AVI. As a consequence of long-term or short-term variation in patient AV conduction characteristics, HF therapy (e.g., CRT, LV-only or BiV pacing, SSP or MSP) in accordance with a previously optimized AVD may no longer be effective or optimal.

The present inventors have recognized several technical challenges in cardiac pacing therapy for treating HF. One challenge has to do with individualized and dynamic HF therapy to address inter-patient differences in cardiac pacing therapy efficacy, as well as intra-patient variation over time in cardiac pacing efficacy at least due to long-term and short-term changes in patient physiological or functional conditions. For example, patient cardiac status such as intrinsic AV conduction characteristics may vary at different heart rate or heart rate ranges. A HF therapy optimized based on patient prior conditions or at one heart rate range may not be optimal under a different condition or heart rate range. Another challenge pertains to efficient acquisition of information of patient cardiac status, such as intrinsic AV conduction characteristics, for use in optimizing individualized HF therapy. A conventional technique for acquiring patient cardiac status information includes monitoring a physiologic signal, and sampling a physiologic parameter (e.g., an AV conduction characteristic) at a predetermined fixed time interval or rate. In this document, the sampling of a physiologic parameter refers to measuring the physiologic parameter according to a schedule, such as at a particular time or a periodic sampling rate (e.g., performing a measurement once every 5 minutes). For example, intrinsic AVI can be sampled once per minute. A therapy parameter, such as AVD, can be adjusted accordingly using the sampled AVI value. Conventional periodic sampling at a fixed interval or rate may have several disadvantages. First, in some instances, it may not effectively capture the changes in patient cardiac condition. For example, although HF patients may have their heart rates more frequently hovering within a relatively narrow range (hereinafter referred to as "frequent heart rates," e.g., 50-80 bpm) due to their impaired cardiac functional capacity, other heart rates (hereinafter referred to as "rare heart rates," e.g., >100 bpm) may occasionally occur under certain circumstances. The heart rate can include intrinsic heart rates in the absence of atrial pacing. Alternatively, the heart rates can be detected during atrial pacing. Such atrial-paced heart rates are substantially equal to atrial pacing rates. To optimize HF therapy under different cardiac status such as different heart rates, stimulation parameters can be re-optimized for those "rare heart rates." However, conventional periodic sampling at a fixed interval or rate may not reliably capture the AV conduction characteristics corresponding to the "rare heart rates," at least because the "rare heart rates" may occur outside the predetermined sampling intervals. Instead, the sampled AV conduction characteristics may likely correspond to "frequent heart rates." This may not only prevent or delay therapy re-optimization for the "rare heart rates," but can waste system resources and battery power due to unintended repetitive sampling of AV conduction characteristics for the "frequent heart rates."

Another challenge pertains to a guarantee of adequate ventricular pacing therapy (e.g., CRT). During a therapy optimization process, pacing therapy may have to be suspended, albeit temporarily, so as to provide event sensing and evaluation of intrinsic AV conduction characteristics. Frequent suspension of pacing for AVI reevaluation may adversely affect patient outcome, particularly in pacing-dependent patients. With regard to the conventional periodic sampling at a fixed interval or rate, although increasing the rate (or, decreasing the interval) of periodic sampling of AV conduction characteristic may increase the likelihood of capturing the "rare heart rates," it may increase the pacing suspension time substantially. For example, by increasing the sampling rate from once per minute to once per 30 seconds, the pacing suspension time can be doubled. This may be clinically impactful to pacing-dependent patients. Moreover, the higher sampling rate may result in substantially more repetitive sampling and processing the AV conduction characteristics for the "frequent heart rates," exacerbating inefficient system resource use and wasting battery power.

The present document provides technical solutions to the above-identified challenges in cardiac pacing therapy for HF, and can improv the medical technology of device-based heart failure patient management. Among other things, the present document provides apparatus and methods for updating stimulation parameters, including stimulation timing parameters such as AVD values corresponding to different heart rates or heart rate ranges. The dynamic parameter update discussed herein may also apply to other stimulation parameters, such as for determining a stimulation site or a stimulation mode. The dynamic parameter update can tailor cardiac pacing therapy to an individual patient, as well as to particular patient physiological or functional conditions. In some examples, the stimulation parameter values (e.g., AVD) corresponding to a multitude of patient conditions may be arranged in a stimulation parameter table. Adjustment of stimulation timing, stimulation site, or stimulation mode based on patient conditions may help tailor cardiac pacing therapy to individual patient under specific physiologic conditions. In an example, the dynamic adjustment may be specific to a heart rate or heart rate range, or on a beat-to-beat basis. In addition to improved therapy efficacy and patient outcome, the systems and methods discussed herein may also reduce healthcare cost associated with HF management. The present document also provides identification of the conditions that may affect stimulation timing and therapy efficacy. This may be beneficial for healthcare providers to track patient HF progression, and improve patient management.

This document also discusses a timing control technique to time AV conduction characteristic measurement for heart rates falling in different heart rate ranges. In an embodiment, separate timers may be provided for a plurality of heart rate ranges, and independently time AV conduction characteristic measurement (e.g., enabling or disabling the sampling AV conduction characteristic) for the corresponding heart rate ranges. When a heart rate (intrinsic heart rate, or heart rate during atrial pacing) is detected in a particular heart rate range, the AV conduction characteristic can be measured only when the timer, corresponding to the particular heart rate range, times out. The timers can each be programmed with a respective timer duration. The timers can operate independently, with their own reset time and expiration time. When a first timer blocks sampling AV conduction characteristic for a sensed heart rate falling in a first heart rate range, a second timer may still enable sampling AV conduction characteristic for a sensed heart rate falling in a different second heart rate range. Because the "rare heart rates" in HF patients are typically in a different heart rate range than the "frequent heart rates," separate timers can time the sampling of the AV conduction characteristics for the "rare heart rates" and for "frequent heart rates" respectively. Compared to conventional periodic sampling at a fixed interval or rate irrespective of heart rates, the multiple timers for different heart rate ranges as discussed in this document can more reliably capture patient AV conduction characteristics for the "rare heart rates." Additionally, because the sampling of AV conduction characteristic for the "frequent heart rates" is timing-controlled by a timer dedicated to that heart rate range, the repetitive sampling of AV conduction characteristics for the "frequent heart rates" can be substantially reduced. Accordingly, system resources and battery power can be saved, and overall operation cost can be reduced.

In addition to the improvement in the medical technology of device-based heart failure patient management under various patient conditions, the systems, devices, and methods discussed herein may also allow for more efficient device memory usage, such as by storing and updating the stimulation timing parameter that are clinically more relevant to patient long-term and short-term changing conditions. The individualized and dynamically adjusted therapy discussed in this document may not only improve therapy efficacy and patient outcome, but may also save device power and extend battery life. With individualized HF therapy tailored to specific patient conditions, fewer unnecessary interventions or hospitalizations may be scheduled, prescribed, or provided; as a result, overall cost savings may be realized.

FIG. 1 illustrates an example of a patient management system 100 and portions of an environment in which the patient management system 100 may operate. The patient management system 100 may include an ambulatory medical device, such as an implantable medical device (IMD) 110 that may be electrically coupled to a heart 105 through one or more leads 108A-C, and an external system 120 that may communicate with the IMD 110 via a communication link 103. Examples of the IMD 110 may include, but are not limited to, pacemakers, defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The IMD 110 may be coupled to, or may be substituted by a monitoring medical device such as a bedside or other external monitor. In addition to or in lieu of the IMD 110, other ambulatory medical device may be used, which may include subcutaneous medical device such as a subcutaneous monitor or diagnostic device, or external monitoring or therapeutic medical devices such as automatic external defibrillators (AEDs) or Holter monitors; wearable medical devices such as patch-based devices, smart watches, or smart accessories; or a bedside monitor.

The IMD 110 may include a hermetically sealed can 112 that may house an electronic circuit that may sense a physiological signal in the heart 105 and may deliver one or more therapeutic electrical pulses to a target region, such as in the heart, such as through one or more leads 108A-C. The patient management system 100 may include only one lead such as 108B, or may include two leads such as 108A-B.

The lead 108A may include a proximal end that may be connected to IMB 110 and a distal end that may be placed at a target location such as in the right atrium (RA) 131 of the heart 105. The lead 108A may have a first pacing-sensing electrode 141 that may be located at or near its distal end, and a second pacing-sensing electrode 142 that may be located at or near the electrode 141. The electrodes 141 and 142 may be electrically connected to the IMB 110 such as via separate conductors in the lead 108A, such as to allow for sensing of the right atrial activity and optional delivery of atrial pacing pulses. The lead 108B may be a defibrillation lead that may include a proximal end that may be connected to IMD 110 and a distal end that may be placed at a target location such as in the right ventricle (RV) 132 of heart 105. The lead 108B may have a first pacing-sensing electrode 152 that may be located at distal end, a second pacing-sensing electrode 153 that may be located near the electrode 152, a first defibrillation coil electrode 154 that may be located near the electrode 153, and a second defibrillation coil electrode 155 that may be located at a distance from the distal end such as for superior vena cava (SVC) placement. The electrodes 152 through 155 may be electrically connected to the IMD 110 such as via separate conductors in the lead 108B. The electrodes 152 and 153 may allow for sensing of a ventricular EGM and may optionally allow delivery of one or more ventricular pacing pulses, and electrodes 154 and 155 may allow for delivery of one or more ventricular cardioversion/defibrillation pulses. In an example, the lead 108B may include only three electrodes 152, 154 and 155. The electrodes 152 and 154 may be used for sensing or delivery of one or more ventricular pacing pulses, and the electrodes 154 and 155 may be used for delivery of one or more ventricular cardioversion or defibrillation pulses. The lead 108C may include a proximal end that may be connected to the IMB 110 and a distal end that may be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C may include an electrode 161 that may be located at a distal end of the lead 108C and another electrode 162 that may be located near the electrode 161. The electrodes 161 and 162 may be electrically connected to the IMB 110 such as via separate conductors in the lead 108C such as to allow for sensing the LV EGM and optionally allow delivery of one or more resynchronization pacing pulses from the LV. Additional electrodes may be included in or along the lead 108C. In an example, as illustrated in FIG. 1, a third electrode 163 and a fourth electrode 164 may be included in the lead 108. In some examples (not shown in FIG. 1), at least one of the leads 108A-C, or an additional lead other than the leads 108A-C, may be implanted under the skin surface without being within at least one heart chamber, or at or close to heart tissue.

The IMB 110 may include circuitry that may sense a physiological signal. The physiological signal may include an EGM or a signal representing mechanical function of the heart 105. The hermetically sealed can 112 may function as an electrode such as for sensing or pulse delivery. For example, an electrode from one or more of the leads 108A-C may be used together with the can housing 112 such as for unipolar sensing of an EGM or for delivering one or more pacing pulses. A defibrillation electrode from the lead 108B may be used together with the can housing 112 such as for delivering one or more cardioversion/defibrillation pulses. In an example, the IMB 110 may sense impedance such as between electrodes located on one or more of the leads 108A-C or the can housing 112. The IMB 110 can be configured to inject current between a pair of electrodes, sense the resultant voltage between the same or different pair of electrodes, and determine impedance using Ohm's Law. The impedance may be sensed in a bipolar configuration in which the same pair of electrodes may be used for injecting current and sensing voltage, a tripolar configuration in which the pair of electrodes for current injection and the pair of electrodes for voltage sensing may share a common electrode, or tetrapolar configuration in which the electrodes used for current injection may be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiological signal may be sensed from one or more physiological sensors that may be integrated within the IMD 110. The IMD 110 may also be configured to sense a physiological signal from one or more external physiological sensors or one or more external electrodes that may be coupled to the IMD 110. Examples of the physiological signal may include one or more of ECG, intracardiac EGM, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiological response to activity, posture, respiration, body weight, or body temperature, among others.

In certain examples, the system 100 may include one or more leadless sensors not being tethered to the IMD 110 via the leads 108A-C. The leadless ambulatory sensors can be configured to sense a physiological signal and wirelessly communicate with the IMD 110. In some examples, the IMD 110 may be a leadless medical device. Unlike a tethered device such as the IMD 110 as illustrated in FIG. 1, a leadless medical device requires no lead, wire, or tether extended between the electrodes and the device body. The leadless medical device may include an anchoring or fixation mechanism for positioning the device body on a target implant side, such as an endocardial surface of one of a left ventricle, a right ventricle, a left atrium, or a right atrium, or an epicardial surface of a portion of the heart. The leadless medical device may be delivered transvenously and positioned within a blood vessel on the heart, such as a coronary vein, where one or more electrodes on the leadless medical device may be directly or indirectly in contact with the epicardial surface of the heart. An example of such an leadless medical device may include the leadless cardiac pacemaker (LCP) disclosed in the commonly assigned U.S. Patent Application Publication US2016/0051823 by Maile et al., entitled "LEADLESS CARDIAC PACEMAKER HAVING A SENSOR WITH A LOWER POWER MODE," which is hereby incorporated by reference in its entirety.

The arrangement and functions of these leads and electrodes are described above by way of example and not by way of limitation. Depending on the need of the patient and the capability of the implantable device, other arrangements and uses of these leads and electrodes are possible.

The patient management system 100 may include a dynamically controlled stimulation circuit 113. The dynamically controlled stimulation circuit 113 may determine therapy parameters dynamically according to patient present physiological or functional condition. Patient conditions such as patient health status, HF progressions, remodeling or decompensation, heart rate, postures, posture transitions, physical activities, sleep/awake status, medication, hydration, diet, among other factors, may affect cardiac electrical and mechanical properties, and consequently affect HF therapy efficacy. In an example, the dynamically controlled stimulation circuit 113 may determine a stimulation site such as between a LV-only pacing and a BiV pacing, or a stimulation mode such as between a SSP and MSP, based on the sensor input. The dynamically controlled stimulation circuit 113 may independently time AV conduction characteristic measurement using separate timers for a plurality of heart rate ranges. The timers can be programmed with respective timer durations, and can operate independently with respective reset and expiration time. The multiple independently operated timers for different heart rate ranges can be more effective in capturing patient AV conduction characteristics for the "rare heart rates." Examples of the dynamically controlled stimulation circuit 113 are described below, such as with reference to FIG. 2.

The external system 120 may allow for programming of the IMB 110, and receiving information from the IMD 110, via a communication link 103. The external system 120 may include a local external IMD programmer. The external system 120 may include a remote patient management system that may monitor patient status or adjust one or more therapies such as from a remote location. The remote patient management system may evaluate collected patient data and provide alert notifications, among other possible functions. In an example, the remote patient management system may include a centralized server acting as a central hub for collected patient data storage and analysis. The server can be configured as a uni-, multi- or distributed computing and processing system. The remote patient management system may additionally or alternatively include one or more locally configured clients or remote clients securely connected to the server. Examples of the clients may include personal desktops, notebook computers, mobile devices, or other computing devices. System users, such as clinicians or other qualified medical specialists, may use the clients to securely access stored patient data assembled in the database in the server.

The communication link 103 may include one or more of an inductive telemetry link, a radio-frequency telemetry link, or a telecommunication link, such as an internet connection. The communication link 103 may provide for data transmission between the IMB 110 and the external system 120. The transmitted data may include, for example, real-time physiological data acquired by the IMD 110, physiological data acquired by and stored in the IMD 110, therapy history data or data indicating IMD operational status, programming instructions to the IMD 110 such as to configure the IMD 110 to perform one or more actions including, for example, data acquisition, device self-diagnostic test, or therapy delivery.

The dynamically controlled stimulation circuit 113 may be implemented at the external system 120 such as using data extracted from the IMB 110 or data stored in a memory within the external system 120. Portions of the dynamically controlled stimulation circuit 113 may be distributed between the IMD 110 and the external system 120.

Portions of the IMB 110 or the external system 120 may be implemented using hardware, software, or any combination of hardware and software. Portions of the IMB 110 or the external system 120 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals. While described with reference to the IMD 110, the patient management system 100 could include a subcutaneous medical device (e.g., subcutaneous ICD, subcutaneous diagnostic device), wearable medical devices (e.g., patch based sensing device), or other external medical devices.

Figure 2:
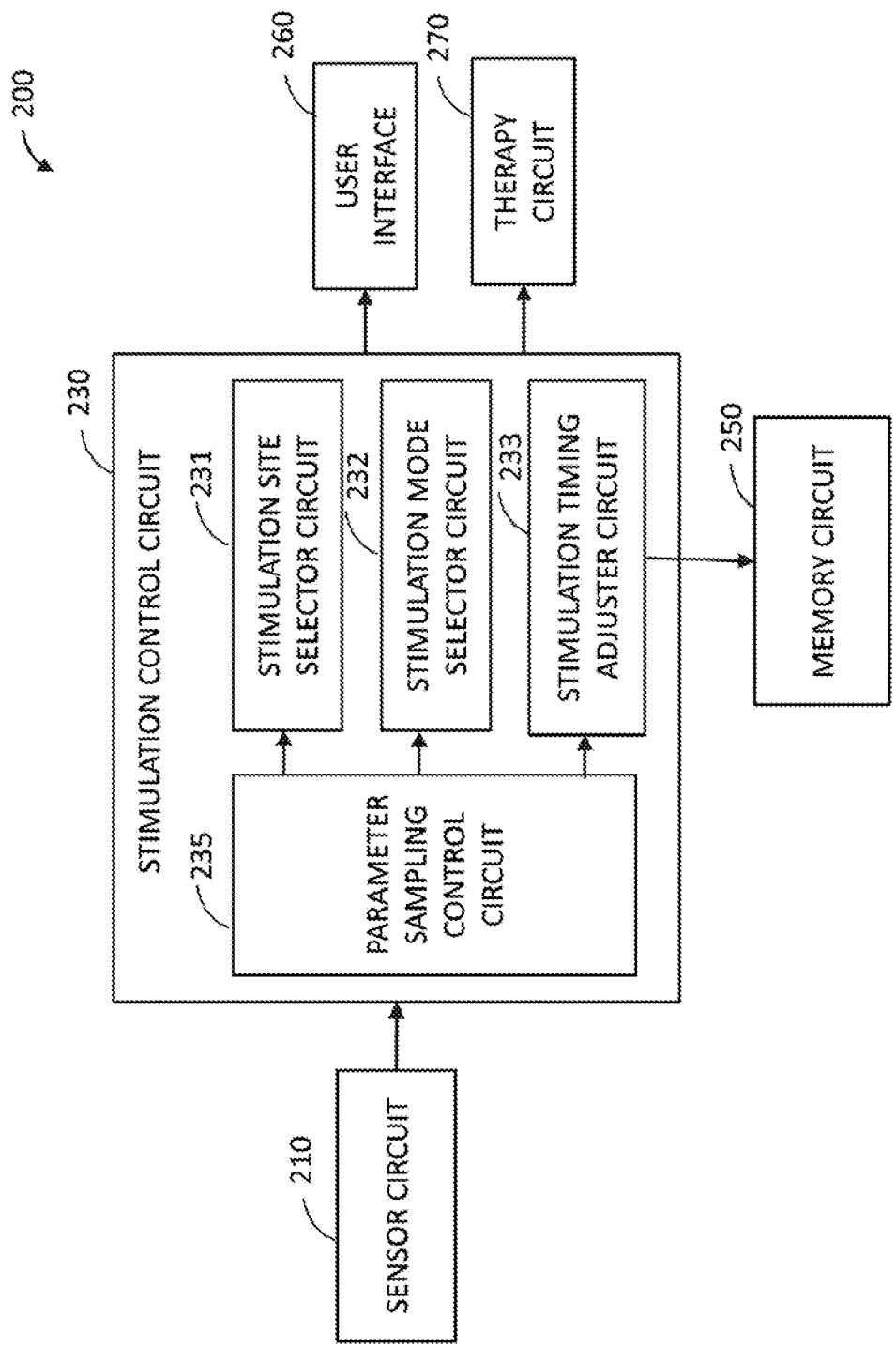
FIG. 2 illustrates an example of a dynamically controlled cardiac stimulation system configured to program and deliver electrostimulation to treat HF or other cardiac diseases.

FIG. 2 illustrates an example of a dynamically controlled cardiac stimulation system 200. The dynamically controlled cardiac stimulation system 200 can be configured to provide diagnostic information including, for example, changes of cardiac status at various patient physiological or functional conditions, and recommend therapy parameters values such as timing, site, or mode of cardiac stimulation. The dynamically controlled cardiac stimulation system 200 may include one or more of a sensor circuit 210, a stimulation control circuit 230, a memory circuit 240, and a user interface 260. In some examples, the system 200 may additionally include a therapy circuit 270 configured to deliver a therapy such as cardiac stimulation. At least a portion of the cardiac monitoring system 200 may be implemented in an AMD, such as the IMD 110, or distributed between an AMD or and an external system such as the external system 120.

The sensor circuit 210 may include a sense amplifier to sense a cardiac signal. The cardiac signal may be sensed from different heart chambers, such as one or more of the RA, the RV, the left atrium (LA), or the LV. The cardiac signal may be sensed when the heart undergoes an intrinsic rhythm such as a sinus rhythm, or when the heart is stimulated in accordance with a stimulation protocol, such as pacing at an atrium, a ventricle, or other sites at a specified rate or timing sequence. Examples of the cardiac signal may include cardiac electrical signals such as ECGs sensed non-invasively from body surface, subcutaneous ECGs sensed from subcutaneously placed electrodes, or intracardiac EGMs sensed from electrodes on one or more of the leads 108A-C or the can housing 112. By way of example and not limitation, atrial activation (denoted by AS) may be sensed using a sensing vector comprising one of the atrial electrodes 141 or 142, right ventricular activation (denoted by RVS) may be sensed using a sensing vector comprising one of the RV electrodes 152-154, and left ventricular activation (denoted by LVS) may be sensed using a sensing vector comprising one of the LV electrodes 161-164.

Additionally or alternatively, the cardiac signals may include signals indicative of cardiac mechanical activities or patient hemodynamic status. In an example, the cardiac signal may include a signal sensed from an accelerometer or a microphone configured to sense heart sounds in a patient. In an example, the cardiac signal may include a cardiac or thoracic impedance signal. The cardiac mechanical signals may include blood pressure sensor signals or any other sensor signals indicative of cardiac mechanical activities or hemodynamic status.

In some examples, the sensor circuit 210 may simultaneously or sequentially sense two or more cardiac signals from different sites of a heart chamber, such as multiple sites at the LV. The sensor circuit 210 may sense LV EGMs from two or more LV sites using respective sensing vectors. An example of the LV sensing vector may include a bipolar sensing vector, such as between a pair of electrodes selected among 161-164. Alternatively, the LV sensing vector may be between one of the electrodes 161-164 and another electrode positioned on a different chamber or on a different lead (such as one of electrodes 152-155 on the RV lead 108B, or electrodes 141 or 142 on the RA lead 108A). Another example of the LV sensing vector may include a unipolar sensing vector such as between one of the electrodes 161-164 and the can housing 112.

The sensor circuit 210 may process the sensed cardiac signal, including amplification, digitization, filtering, or other signal conditioning operations. From the processed cardiac signal, the sensor circuit 210 may detect signal features, or perform measurements that indicate patient cardiac condition or therapy efficacy, or a complication introduced by the stimulation. Examples of the signal features may include temporal or morphological features indicative of intrinsic cardiac activity such as a P wave, Q wave, R wave, QRS complex, or T wave that may be detected from a surface ECG, a subcutaneous ECG, or an intracardiac EGM, timing and intensity of evoked cardiac activity such as evoked electrical or mechanical activation in response to an electrostimulation of the heart. Examples of the timing measurement may include a time delay between cardiac activations sensed at different heart chambers (e.g., PRI or AVI between an atrium and a ventricle, or RV to LV sensed interval), or between different pacing sites (e.g., sensing delay among various LV sites).

The sensor circuit 210 may additionally receive information about patient long-term or short-term physiological or functional conditions. Changes in long-term or short-term patient conditions may affect cardiac electrical and mechanical properties and patient hemodynamic responses. As a result, a therapy may be less effective if not timely and properly adjusted to accommodate the changing patient condition. Physiological signals, such as cardiac, pulmonary, neural, or biochemical signals, may be received at the sensor circuit 210. Examples of the physiological signals may include ECG, intracardiac EGM, a heart rate signal, a heart rate variability signal, a cardiovascular pressure signal, a heart sounds signal, a respiratory signal, a thoracic impedance signal, a respiratory sounds signal, or blood chemistry measurements or expression levels of one or more biomarkers. Examples of the functional signals may include patient posture, gait, balance, or physical activity signals, among others. The sensor circuit may sense the functional signals using a motion sensor, such as an accelerometer, gyroscope (which may be a one-, two-, or three-axis gyroscope), magnetometer (e.g., a compass), inclinometers, goniometers, altimeters, electromagnetic tracking system (ETS), or a global positioning system (GPS) sensor, among others. In another example, the functional signal may include information about sleep state signal, such as sleep or awake state, frequency or duration of sleep position switch, sleep incline, or other indicators of sleep quality. In another example, the functional signal may include information on food or drink intake (e.g., swallow), coughing or aspiration detection. In some examples, information about patient physiological or functional conditions may be stored in a storage device, such as an electronic medical record (EMR) system, and the sensor circuit 210 can be configured to receive the patient condition from the storage device in response to a user input or triggered by a specific event.

In some examples, the sensor circuit 210 may receive information about patient medical history, medication intake, hospitalization, surgical procedures, cardiac remodeling, worsening heart failure events such as heart failure decompensation, or HF comorbidities. In some examples, the sensor circuit 210 may receive device implant information, such as position of an implantable lead. For example, an LV lead 108C may be implanted at free wall, anterior, lateral, or posterior, among other possible LV positions. LV lead location may affect the therapy efficacy, and be used for determining the stimulation site, mode, and timing parameter. In some examples, the sensor circuit 210 may additionally include patient echocardiography-derived measurements, such as ejection fraction, cardiac contractility, cardiac timing, or aortic velocity, among other hemodynamic parameters or other clinical diagnostics.

The stimulation control circuit 230 may generate diagnostics about changes of cardiac status at a particular patient physiological or functional condition as received from the sensor circuit 210, and recommend therapy parameter values including, for example, timing, site, or mode of cardiac stimulation. The stimulation control circuit 230 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The stimulation control circuit 230 may include circuit sets comprising one or more other circuits or sub-circuits, such as one or more of a parameter sampling control circuit 235, a stimulation site selector circuit 231, a stimulation mode selector 232, and a stimulation timing adjuster circuit 233. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The stimulation site selector circuit 231 can be configured to determine a heart chamber for pacing according to the received patient condition. In an example, the stimulation site selector circuit 231 may select between an LV-only pacing and a BiV pacing. The BiV pacing refers to stimulation of both the LV and RV simultaneously or sequentially with a specified time offset. In some patients, the BiV pacing may offer better cardiac synchrony and cardiac contractility than the LV-only pacing configured for only stimulating the LV. However, a change in patient physiological or functional condition (e.g., a heart rate increase, or a posture transition from supine to standing) may alter AV condition, ventricular contractility, or other cardiac properties. Pacing chamber may need to be switched, among other therapy adjustments, to maintain adequate therapy efficacy. The stimulation site selector circuit 231 may initiate stimulation site assessment in response to a change of patient condition, and determine between an LV-only pacing and BiV pacing based on a heart rate increase, and an indicator of AV conduction abnormality, such as an extension of PRI or AVI or increased irregularity of the PRI or AVI. An example of determining stimulation site between LV-only pacing and BiV pacing in accordance with changes in patient conditions is disclosed in the commonly assigned U.S. patent application Ser. No. 16/007,094 by Ternes et al., entitled "SYSTEMS AND METHODS FOR DYNAMIC CONTROL OF HEART FAILURE THERAPY," which is hereby incorporated by reference in its entirety.

The stimulation mode selector circuit 232 can be configured to determine between a single site pacing (SSP) and a multisite pacing (MSP) according to the received patient condition. The MSP may be delivered at two or more sites inside, or on an epicardial surface of, one or more heart chambers or tissues surrounding any of the chambers. During MSP, pulse trains may be delivered at the two or more cardiac sites simultaneously, or sequentially with an intra-ventricular delay less than a sensed or paced time interval value of the cardiac cycle. In an example, the stimulation mode selector circuit 232 may initiate stimulation mode assessment in response to a change of patient condition, and determine between SSP pacing and a MSP pacing at two or more LV sites using inter-ventricular intervals measured from RV site to various candidate LV sites, such as those corresponding to the LV electrodes 161-164. The inter-ventricular intervals represent degrees of dyssynchrony between RV and various LV sites. The stimulation mode selector circuit 232 may scan through a plurality of candidate LV electrodes to identify those LV sites with the corresponding inter-ventricular intervals satisfying a specified condition, such as a patient condition-indicated threshold value, and select SSP or MSP based on the candidate electrodes identification. Commonly assigned U.S. patent application Ser. No. 16/007,094 by Ternes et al., entitled "SYSTEMS AND METHODS FOR DYNAMIC CONTROL OF HEART FAILURE THERAPY" discloses a method of determining stimulation mode between SSP and MSP in accordance with changes in patient conditions, the disclosure of which is hereby incorporated by reference in its entirety.

The stimulation timing adjuster circuit 233 can be configured to determine or update a stimulation timing parameter using patient physiological or functional information, such as measurements of AV conduction characteristic. The stimulation timing parameter may be determined or updated at a particular time, or at a particular periodic update rate. The stimulation timing parameter defines the timing sequence for delivering cardiac stimulation (e.g., ventricular pacing). Such timing sequence can be important to ensure therapy efficacy and patient hemodynamic outcome. Examples of the timing parameter may include AVD, VVD, or ILVD. In an example, the stimulation timing adjuster circuit 233 may determine or update AVD using patient intrinsic AVI under the received patient condition. The AVI may be measured directly from the sensed cardiac signal under a specific patient condition. Alternatively, the AVI may be estimated dynamically during pacing. Commonly assigned U.S. patent application Ser. No. 16/007,094 by Ternes et al., entitled "SYSTEMS AND METHODS FOR DYNAMIC CONTROL OF HEART FAILURE THERAPY" discloses a method of AVI estimation during pacing using a combination of the AVD that leads to pseudo-fusion and the stored offset, the description of which is hereby incorporated by reference in its entirety.

In some examples, the stimulation timing adjuster circuit 233 may determine or update a stimulation timing parameter (e.g., AVD) using a weighted combination of (1) a historical stimulation timing parameter value and (2) the determined value of the AV conduction characteristic, each scaled by respective weight factors. In an example, an AVD may be updated recursively using intrinsic AVI values as follows:

$$AVD(n)=a*AVD(n-1)+b*AVI(n) \tag{1}$$

where AVD (n) denotes a newly updated AVD value, AVD (n−1) denotes a historical AVD value prior to the update, and AVI(n) denotes a presently measured or estimated intrinsic AVI value. In an example, the stimulation timing adjuster circuit 233 can adjust one or more of the weight factors "a" or "b" using information of physical activity of the patient. When patient physical activity increases, the intrinsic AVI may change more substantially. Accordingly, AVD may be adjusted to address the change in AVI. In an example, in response to elevated physical activity, the stimulation timing adjuster circuit 233 can decrease the weight factor "a", and/or increase the weight factor "b" such that the AVD is more sensitive to the present AVI.

In an example, the stimulation timing adjuster circuit 233 may determine or update AVD using a combination of an AVI measured at the right ventricle ($AV_R$) and an AVI measured at the left ventricle ($AV_L$). The $AV_R$ represents an interval between an atrial sensed (AS) or atrial paced (AP) activation to a sensed RV activation (RVS). The $AV_L$ represents an interval between an AS or an AP activation to a sensed LV activation (LVS). Commonly assigned U.S. patent application Ser. No. 16/007,094 by Ternes et al., entitled "SYSTEMS AND METHODS FOR DYNAMIC CONTROL OF HEART FAILURE THERAPY" discusses a method of determining AVD using a linear weighted combination of $AV_R$ and $AV_L$, the disclosure of which is hereby incorporated by reference in its entirety.

The parameter sampling control circuit 235 can be configured to independently sample the AV conduction characteristic for a plurality of heart rate ranges. In an embodiment, the parameter sampling control circuit 235 may include separate timers respectively for the plurality of heart rate ranges. The timers can be programmed with respective timer durations, and operate independently with respective reset and expiration time. The timers can enable or disable measurement of AV conduction characteristic for the corresponding heart rate ranges based on the states of the respective timer (e.g., whether or not the timer has timed out or expired). For a heart rate (intrinsic heart rate, or heart rate during atrial pacing) detected in a heart rate range, the AV conduction characteristic can be sampled only when the timer, corresponding to the particular heart rate range, times out. For example, when a first timer blocks sampling AV conduction characteristic for a detected heart rate falling in one heart rate range, a different second timer may still enable sampling AV conduction characteristic for a detected heart rate falling in a different heart rate range, provided the second timer has timed out. In some examples, the parameter sampling control circuit 235 may include a global timer having a duration, and the separate timers included in the parameter sampling control circuit 235 may be triggered to enable or disable measurement of AV conduction characteristic in response to an expiration of the global timer. Compared to conventional periodic sampling at a fixed interval or rate irrespective of heart rates, the heart rate-indicated timers can allow the parameter sampling control circuit 235 to more reliably capture patient AV conduction characteristics for the "rare heart rates," while at the same time substantially reduce the repetitive sampling of AV conduction characteristics for the "frequent heart rates." Examples of timing control for sampling AV conduction characteristics using heart-rate indicated timers are discussed below, such as with reference to FIGS. 3-4.

The memory circuit 240 can be configured to store a set of stimulation parameters, such as AVDs. The stimulation timing parameters may correspond to each of a plurality of heart rates or heart rate ranges. In some examples, the stimulation timing parameters may further correspond to other patient conditions such as atrial sensed (AS) events or atrial paced (AP) events, different postures, or different time of a day. In some examples, the memory circuit 240 may store a stimulation parameter table including stimulation timing parameter values and the corresponding plurality of heart rates or heart rate ranges, optionally with one or more other patient conditions (e.g., postures), or information of time of a day, as illustrated in FIG. 5A-5C below.

The stimulation timing adjuster circuit 233, coupled to the memory circuit 240, may search for the received patient condition from the stimulation parameter table, and identify a recommended AVD corresponding to that patient condition. The stimulation timing adjuster circuit 233 may perform dynamic AVD adjustment by switching to the applicable table entry whenever the patient is in that condition. In an example, the AVD may be adjusted on a beat-by-beat basis, or periodically at specified time.

The user interface 260 may include an input device that enables a system user to program the parameters used for electrostimulation or for sensing the cardiac signals. Examples of the input device may include a keyboard, on-screen keyboard, mouse, trackball, touchpad, touchscreen, or other pointing or navigating devices. The input device may enable the system user to activate automated programming of HF therapy, such as automated determination of stimulation site, stimulation mode, and stimulation timing parameters under a specific patient condition. The input device may also enable the system user to confirm, reject, or otherwise modify the automatically determined therapy programming.

The user interface 260 may include a display for display therapy programming such as automatically determined stimulation site, stimulation mode, and stimulation timing parameters. The output unit 230 may include a printing device for producing a hardcopy of the information. The information may be presented in a table, a chart, a trend, a diagram, or any other types of textual, tabular, or graphical presentation formats. Additional information for displaying may include cardiac signals, signal features or measurements (e.g., PRI or AVI) derived from the sensed cardiac signal, information of patient physiological or functional conditions received from the sensor circuit 210, or device status information such as lead impedance and integrity, battery status such as remaining lifetime of the battery, or cardiac stimulation threshold, or complications associated with stimulation at one or more cardiac sites, among others.

The therapy circuit 270 can be configured to generate therapy according to the parameter values generated and recommended by the stimulation control circuit 230. The therapy may include electrostimulation delivered to the pacing sites via one or more of the leads 108A-C and the respectively attached electrodes. The therapy circuit 270 can be configured to deliver LV-only pacing, or BiV pacing. Additionally or alternatively, the therapy circuit 270 can be configured to generate SSP for stimulating one cardiac site, or a MSP for stimulating two or more sites of the heart within the same cardiac cycle. In an example, the MSP may be delivered within the LV. The LV MSP may have a unipolar pacing configuration where only one electrode (e.g., a cathode) is a LV electrode and the other electrode (e.g., an anode) is the IMD can housing 112. In another example, a true bipolar configuration may be used, where both the cathode and anode are LV electrodes. In yet another example, an extended bipolar configuration may be used, where one electrode (e.g., a cathode) is a LV electrode and the other electrode (e.g., an anode) is a RA electrode such as one of the electrodes 141 or 142, or a RV electrode such as one of the electrodes 152-155. In another example, a tripolar configuration may be used, which may include two LV electrodes used jointly as a cathode, or two electrodes such as selected from the RA and RV electrodes used jointly as an anode. In an example, one or more LV electrodes may be distributed in one or more LV leads, catheters, or untethered pacing units.

In some examples, the therapy circuit 270 may initiate or adjust electrostimulation at non-cardiac tissues such as nerve tissues, or other therapy types, such as a cardioversion therapy, a defibrillation therapy, or drug therapy including delivering drug to a tissue or organ. In some examples, the therapy circuit 270 may modify an existing therapy, such as adjust a stimulation parameter or drug dosage.

Figure 3:
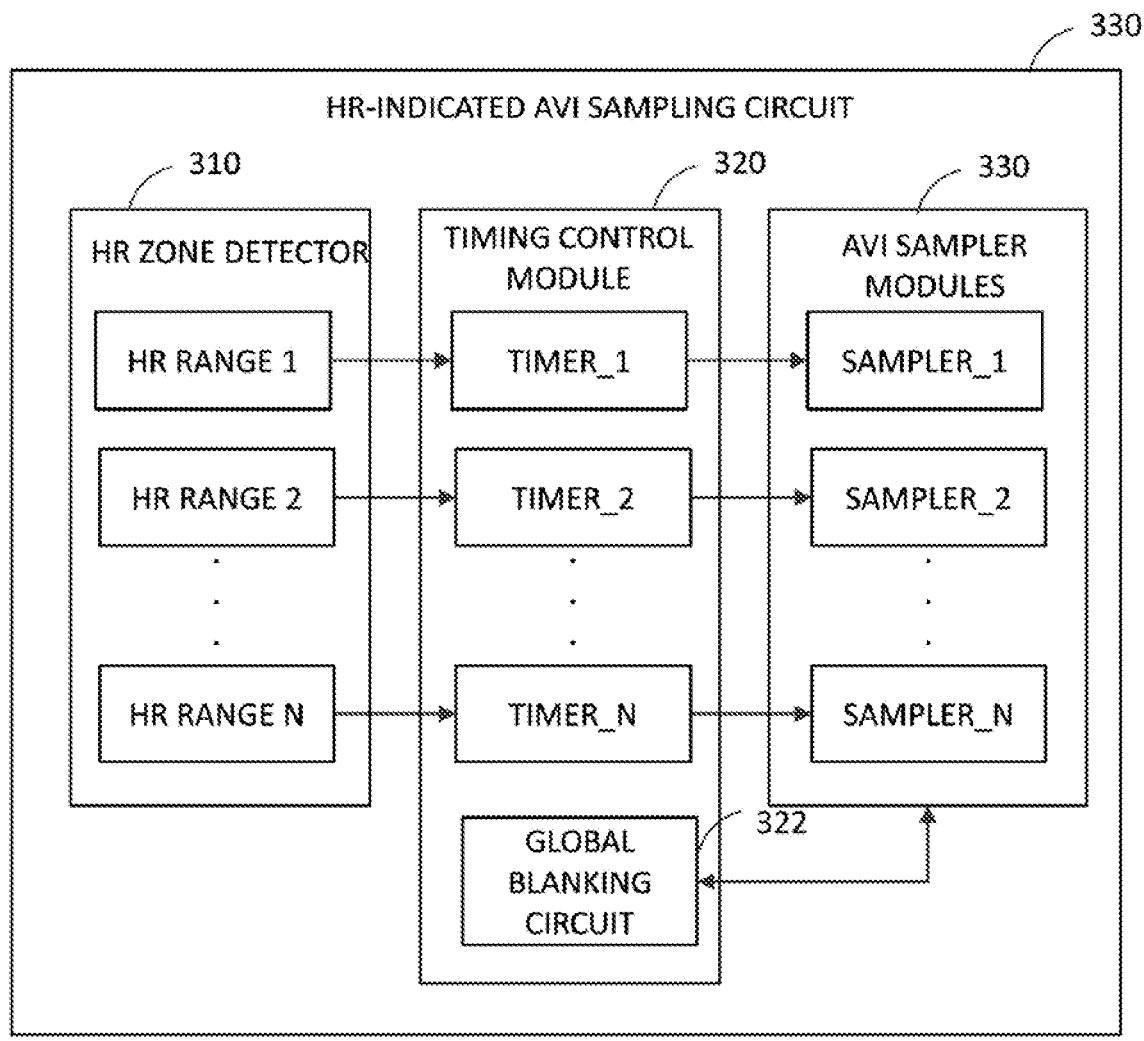
FIG. 3 is a block diagram illustrating an example of a heart rate-indicated AVI sampling control circuit configured to sample AV conduction characteristics for heart rates sensed in a plurality of heart rate ranges.

FIG. 3 is a block diagram illustrating an example of a heart rate-indicated AVI sampling control circuit 300 configured to sample AV conduction characteristics for heart rates detected in a plurality of heart rate ranges. In this document, the sampling of a physiologic parameter refers to measuring the physiologic parameter according to a schedule, such as at a particular time or a periodic sampling rate (e.g., performing a measurement once every 5 minutes). The heart rate-indicated AVI sampling circuit 300, which is an embodiment of the parameter sampling control circuit 235 of the system 200 shown in FIG. 2, can include a HR zone detector 310, a timing control module 320, and AVI sampler modules 330. The HR zone detector 310 can monitor patient heart rate continuously or intermittently, and detect a heart rate in one of a plurality of heart rate ranges HR range 1 (HR_1) through HR range N (HR_N). The heart rate can be an intrinsic heart rate in the absence of atrial pacing. Alternatively, the heart rate can be detected during atrial pacing. Such atrial-paced heart rate is substantially equivalent to atrial pacing rate. The heart rate ranges can be non-overlapping to each other. By way of example and not limitation, HR_1 is <60 bpm, HR_2 is 60-70 bpm, HR_3 is 70-90 bpm, HR_4 is 90-120 bpm, etc.

The timing control module 320 can include a plurality of timers, Timer_1 through Timer_N, corresponding to the HR ranges HR_1 through HR_N. These timers can have respective programmable durations (e.g., Dur_1 through Dur_3, for Timer_1 through Timer_N, respectively), and are configured to independently time the measurement of AV conduction characteristic, such as enabling or disabling the measurement of intrinsic AVI, for the corresponding heart rate ranges. Once an AVI value is measured in the corresponding HR range, the corresponding timer can be reset, and is configured to expire after a timer duration since the reset time. The timers can have different reset and expiration time. As a result, when a first timer (e.g., Timer_1) blocks sampling an AVI value for a detected heart rate falling in one heart rate range (HR_1) because the first timer has not timed out, a second timer (e.g., Timer_2) may still enable sampling an AVI value for a detected heart rate falling in a different heart rate range (e.g., HR_2), provided the second timer has timed out.

The AVI sample modules 330 can include a plurality of sampler modules, Sampler_1 through Sampler_N, corresponding to the Timer_1 through Timer_N. The sampler modules are each configured to sample AV conduction characteristic (e.g., measuring AVI values) during a particular time period or a time window for the heart rates detected in the corresponding hear rate range, while at other times can block AVI sampling for the heart rates detected in the corresponding heart rate range. In an example, when a heart rate is sensed in a heart rate range HR_k, the corresponding sampler module, Sampler_k, can sample AVI only when the corresponding timer, Timer_k, times out. That is, Sampler_k follows a sampling control mechanism to enable AVI measurement only when (1) a heart rate is detected in the range HR_k; and (2) the Timer_k is in a timeout or expired state. Examples of independent timing control of sampling AVI using multiple timers for a plurality of heart rate ranges are discussed below with reference to FIG. 4. Such a timing control mechanism can be more effective in capturing patient AV conduction characteristics for the "rare heart rates," and at the same time can substantially reduce the repetitive sampling of AV conduction characteristics for the "frequent heart rates."

Because the AVI sampler modules 330 can enable AVI sampling and AVD update only when the corresponding heart rate-indicated timer has timed out after a programmed timer duration has elapsed, the timer duration, among other things, can therefore determine a rate of periodic AVI sampling and AVD update. In an example, the timer durations for different heart rate ranges can be identical. For example, Dur1=Dur2=Dur3=10 minutes. Alternatively, at least some timer durations are distinct from each other. In an example, a higher heart rate range can be associated with a shorter timer duration for the corresponding timer, thus more frequent AVI sampling, than a lower heart rate range. For example, a timer corresponding to a heart rate range of 100-120 bpm can have a shorter duration than another timer corresponding to a heart rate range of 70-80 bpm. Because HF patients are more likely to develop conduction abnormalities at higher heart rate and thus changes in AV conduction characteristic, a shorter timer duration (or equivalently more frequent evaluation of AVI) can ensure timely capture the changes in AVI and adjust of therapy accordingly (e.g., via an updated AVD).

In some examples, the timer duration can be determined based on a prevalence indicator of the heart rates in each HR range. The prevalence indicator represents an occurrence rate of the heart rates falling in a HR range. For a HR range with more prevalent heart rates, a longer timer duration may be programmed to the corresponding timer. Accordingly, for a heart rate range with more prevalently detected heart rates (or the "frequent heart rates"), a longer timer duration can reduce AVI sampling and AVD update. Due to their reduced cardiac functional capacity, heart failure patients generally have a narrower intrinsic heart rate range than healthy subjects. For example, heart rates are more prevalently observed in a hear rate range of 50-80 bpm than a higher rate range of 100-120 bpm. A longer timer duration for a heart rate range of "frequent heart rates" and a shorter timer duration for a heart rate range of "rare heart rates" can be advantageous, as the system resources can be saved for sampling the AVI and updating the AVD for the less prevalent, "rare heart rates." It may also help reduce repetitive sampling of AVI for the "frequent heart rates" at least because the AVD less likely needs to be updated for the frequent heart rates.

In some examples, at least some timer durations can be updated. The update can occur periodically at a specified time or periodicity, or in response to a trigger event. In some examples, the timing or frequency for updating the timer durations can be automatically determined.

The timing control module 320 may additionally include a global blanking circuit 322 configured to generate a global blanking period ($T_B$) immediately following an AVI measurement carried out by any sampler in the AVI sampler modules 330. In an example, the global blanking period $T_B$ can be approximately 1 minute. During the global blanking period, AVI measurement in all HR ranges can be disabled, regardless of the heart rate or the state of any timer (whether or not timed out). Also immediately following the AVI measurement such as by the Sampler_k, the corresponding timer Timer_k can be reset to its duration Dur_k. Timer_k then counts down as its duration Dur_k elapses, and subsequent AVI measurement is disabled for any heart rate falling in the range HR_k, until the Timer_k expires. In contrast to the global blanking period $T_B$ that affects all samplers, a reset of a particular timer (e.g., Timer_k) has a blanking effect only on the corresponding sampler (e.g., Sampler_k), and does not block other samplers from sampling the AVI.

In some examples, the heart rate-indicated AVI sampling circuit 300 may include a global timer having a duration. The samplers Sampler_1 through Sampler_N may be triggered to enable or disable measurement of AV conduction characteristic in response to an expiration of the global timer. In an example, the global timer can operate in a similar fashion as one of the Timers_1 through Timer_N.

Figure 4:
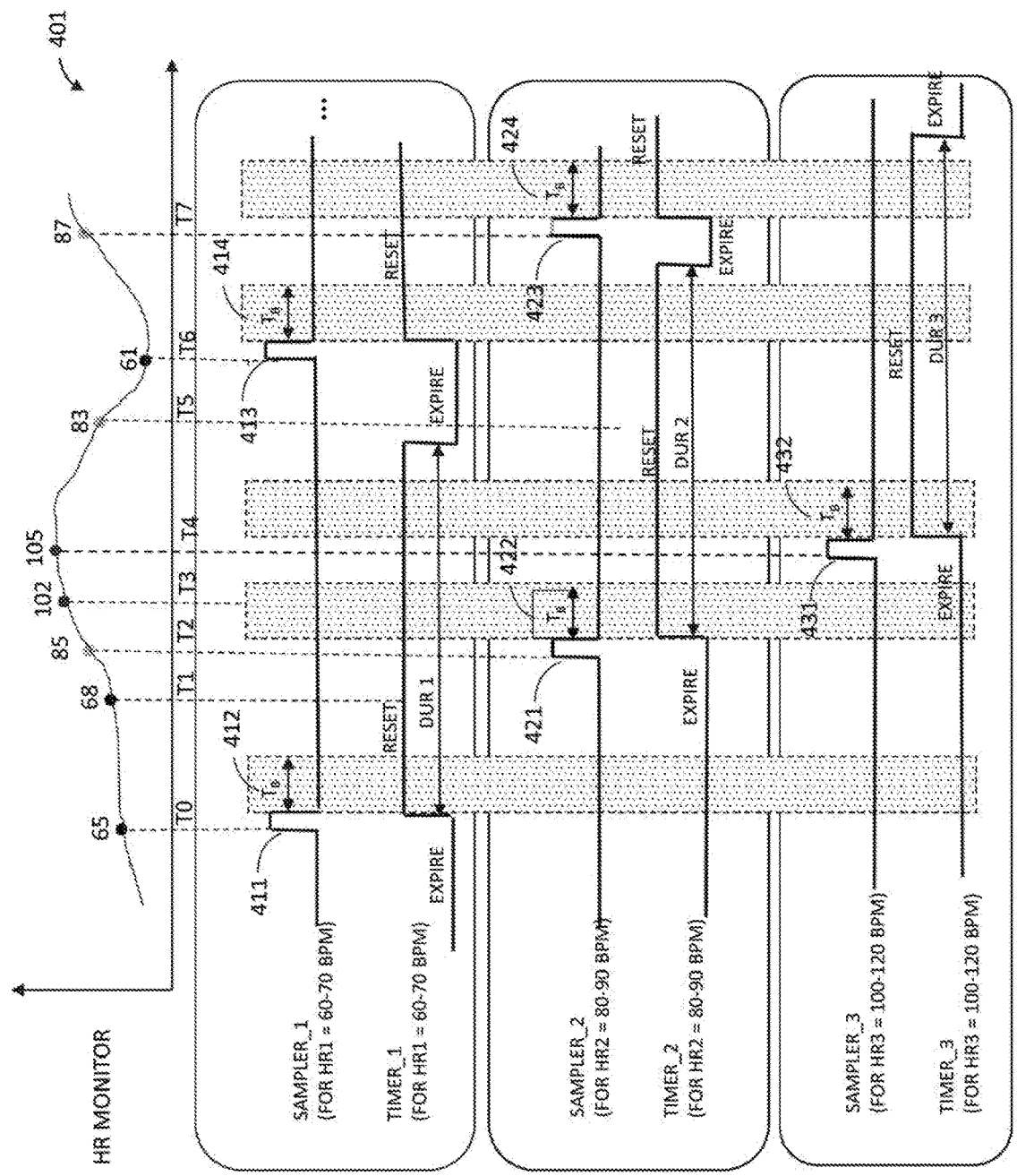
FIG. 4 is a timing diagram illustrating an exemplary sequence of events during sampling of AVI values and updating AVD for respective heart rate ranges.

FIG. 4 is a diagram illustrating, by way of example and not limitation, events during sampling of AVI values and updating AVD for respective heart rate ranges. For the purpose of illustration, three non-overlapping HR ranges are shown: HR_1 of 60-70 bpm, HR_2 of 80-90 bpm, and HR_3 of 100-120 bpm. Corresponding to the heart rate ranges HR_1 through HR_3, AVI samplers Sampler_1 through Sampler_3 can independently sample AVI values during a particular time period or a time window. Each timer has a pre-determined timer duration, such as Dur1 for HR_1, Dur2 for HR_2, and Dur3 for HR_3. In an example, all timer durations are identical. Alternatively, the timer duration can be different across different heart ranges. In an example, a timer for a higher heart rate range has a shorter duration (thus more frequent AVI reevaluation and AVD update) than a timer for a lower heart rate range. Each timer can be reset upon sampling an AVI value in the corresponding HR range, and configured to expire after the timer duration has elapsed.

Heart rates can be continuously or intermittently monitored, and a heart rate signal 401 can be generated using the parameter sampling control circuit 300. The heart rates can be intrinsic heart rates in the absence of atrial pacing. Alternatively, the heart rates can be detected during atrial pacing. Such atrial-paced heart rates are substantially equivalent to atrial pacing rates. Initially, all timers, including Timer_1 through Timer_3, are timeout or expired. At time T0, a heart rate of 65 bpm is detected in HR_1. Because Timer_1 is in a timeout state, Sampler_1 is triggered to open an window 411 to sample an intrinsic AVI value $AVI_{11}$, during which ventricular pacing (e.g., CRT therapy) can be temporarily suspended. The measured $AVI_{11}$ can then be used to update AVD for HR_1, such as using Equation (1). The window opened for intrinsic AVI measurement may be one cardiac cycle. Alternatively, the window may open to sample multiple AVI values in two or more cardiac cycles, either continuously or intermittently.

Immediately following the AVI measurement, a global blanking period 412 can be generated and applied. During the global blanking period 412 with a duration of $T_B$, AVI measurement in all HR ranges, including HR_1, HR_2, and HR_3, are disabled. In an example, $T_B$ is approximately 1 minute. Also immediately following the AVI measurement at 411, Timer_1 can be reset. This disables Sampler_1 from sampling AVI for any heart rates detected in HR_1. However, resetting of Timer_1 has no impact on other samplers to sample AVI in the corresponding heart rate ranges, provided the heart rate and timer state conditions are met in those heart rate ranges.

At T1, HR of 68 bpm is sensed in HR_1. Since it occurs before Timer_1 gets expired, no AVI window can be opened, and no AVD update is carried out for HR_1. At T2, HR of 85 bpm is sensed in HR_2. The corresponding Timer_2 is in an timeout state, so Sampler_2 is triggered to open a window 421 to measure an intrinsic AVI value ($AVI_{21}$), while the ventricular pacing is temporarily suspended. The $AVI_{21}$ can then be used to update AVD for HR_2. Immediately following the AVI measurement at 421, a global blanking period 422 can be applied to block AVI measurement in any HR ranges during $T_B$, and Timer_1 is reset to block AVI measurement only in HR_2 during Dur2.

At T3, HR of 102 bpm is sensed in HR_3. Although Timer_3 is in a timeout state, the detected HR occurs falls within the global blanking period 422. Therefore, no AVI window can be opened, and no AVD update would occur for HR_3.

At T4, HR of 105 bpm is sensed in HR_3, and it does not fall within any global blanking period. Because the corresponding Timer_3 is in a timeout state, the Sampler_3 is triggered to open a window 431 to measure an intrinsic AVI value ($AVI_{31}$), during while the ventricular pacing is temporarily suspended. The $AVI_{31}$ can then be used to update AVD for HR_3. Immediately following the AVI measurement at 431, a global blanking period 432 is applied to block AVI measurement in any HR ranges during $T_B$, and Timer_3 is reset to block AVI measurement only in HR_3 during Dur3.

At T5, HR of 83 bpm is sensed in HR_2. However, Timer_2 has not yet expired at the detection of this heart rate. Therefore, no AVI window can be opened, and no AVD update would occur for HR_2.

At T6, HR of 61 bpm is sensed in HR_1. At this moment, Timer_1 has expired. Therefore, the Sampler_1 is triggered to open a window 413 to measure an intrinsic AVI value ($AVI_{12}$). The $AVI_{12}$ can then be used to update AVD for HR_1. Immediately following the AVI measurement at 413, a global blanking period 414 can be generated to block AVI measurement in any HR ranges during $T_B$, and Timer_1 is reset to block AVI measurement only in HR_1 for a duration Dur1.

At T7, HR of 87 bpm is sensed in HR_2. At this moment, Timer_2 has expired. Therefore, the Sampler_2 is triggered to open a window 423 to measure an intrinsic AVI value ($AVI_{22}$) while the ventricular pacing is temporarily suspended. The $AVI_{22}$ can then be used to update AVD for HR_2. Immediately following the AVI measurement at 423, a global blanking period 424 can be generated to block AVI measurement in any HR ranges during $T_B$, and Timer_2 is reset to block AVI measurement only in HR_2 for a duration Dur2.

As illustrated in FIG. 4, with the multiple, heart rate-indicated timers Timer_1 through Timer_3 and the sampling control mechanism discussed herein, AVI values corresponding to "rare heart rates" in HR ranges HR_2 or HR_3 can be reliably sampled, while repetitive sampling of AVI values corresponding to "frequent heart rates" (e.g., in HR_1) can be effectively avoided or reduced.

FIGS. 5A-5C are diagrams illustrating patient condition-indicated stimulation parameter values, which can be stored in a memory for dynamic cardiac pacing. The stimulation parameters can be stored in a table, such as table 510, 520, or 530, that includes recommended stimulation timing values along with one or more corresponding patient conditions. Each table entry may include a recommended AVD value under a corresponding patient condition. By way of example and not limitation, FIG. 5A illustrates a stimulation parameter table 510 that includes stimulation timing values, such as AVD values, with corresponding heart rate ranges (HR), and atrial activation mode as either atrial sensed (AS) event or atrial paced (AP) events. The AVD for an AS event is referred to a sensed AVD, and the AVD for an AP event is referred to a paced AVD. FIG. 5B illustrates a stimulation parameter table 520, which is a variant of the Table 510 augmented by patient postures. By way of example, the postures included in the Table 520 include supine, sitting, or standing postures. FIG. 5C illustrates a stimulation parameter table 530, which is another variant of the Table 510 augmented by information of time of a day, such as a daytime or a nighttime. Alternatively, the time of a day may include a number of time periods during a day within a 24-hour period. In various examples, table 510, 520, or 530 may be augmented to include other patient conditions, such as activity (walking or running,) sleeping, diet, hydration, medication intake, heart rate, heart rate variability, arrhythmic events (e.g., atrial fibrillation, ventricular tachycardia, premature ventricular contractions, post arrhythmia). Various combination or permutations of patient conditions can be implemented in a stimulation parameter table similar to the table 510-530, which is within the scope of the present document. These patient conditions, individually or in combination, may affect cardiac tissue properties and patient hemodynamics. As a result, a therapy programmed under one condition may not be equally effective under a different condition. Different AVD values may be recommended at different patient conditions to achieve desirable therapy efficacy and patient outcome.

In various examples, at least some entries of a stimulation parameter table may additionally or alternatively include recommended values of stimulation timing parameters other than AVD. In an example, the table entry may include a recommended RV-LV delay (VVD) under corresponding patient conditions of heart rate, posture, and atrial activation mode. The VVD represents an offset between an LV pacing pulse and a RV pacing pulse within a cardiac cycle for BiV pacing or CRT therapy such as selected by a system user or determined by the stimulation control circuit 230. In some examples, the VVD can be set to zero such that LV pacing and RV pacing are simultaneously delivered. In another example, at least some table entries may include a recommended intra-LV time offset (ILVD). The ILVD represents an offset between LV pacing pulses separately delivered at different LV sites within a cardiac cycle when a LV MSP is selected by a system user or determined by the stimulation control circuit 230. The LV MSP may be delivered via two or more of the LV electrodes 161-164 as illustrated in FIG. 1.

In various examples, the stimulation parameter table may be augmented to include information in addition to the stimulating timing parameters. In an example, at least some entries of Tables 510-530 may additionally or alternatively include information about stimulation site such as an indication of LV-only pacing or a BiV pacing, or information about stimulation mode such as an indication of SSP or MSP. The augmented table thus provides comprehensive therapy recommendations on stimulation site, mode, and timing values at various patient conditions. In an example, the entries of the augmented table may be constructed as a class structure in the memory circuit 250 that contains values of one or more of the stimulation site, mode, and timing parameters. For example, one table entry may include (AVD, LV-only pacing), and another table entry may include (AVD, BiV pacing, VVD, MSP, ILVD). In an example, one element in a table entry (e.g., AVD value, BiV pacing, or MSP) may be applied to a number of table entries that share a common condition. For example, if BiV pacing is recommended for a condition defined by sitting posture, AS, and HR great than 100 bpm, then BiV pacing may be recommended for all conditions as long as containing a "sitting" posture, regardless of heart rate ranges, or atrial activation mode (AS or AP). In another example, if MSP is recommended for a condition defined by standing posture, AS, and HR within 70-80 bpm, then MSP may be recommended for all conditions as long as containing a "standing" posture, regardless of heart rate ranges, or atrial activation mode.

In some examples, multiple tables of stimulation timing parameter values may be constructed and stored in the memory circuit 250, such as an AVD table containing only AVD values under various patient conditions, a VVD table containing only VVD values under various patient conditions, or an ILVD table containing only ILVD values under various patient conditions. The tables may include different patient physiological or functional conditions. In an example, the stimulation control circuit 230 may refer to the VVD table to determine an optimal VVD value under a specific patient condition when a BiV pacing is selected. In another example, the stimulation control circuit 230 may refer to the ILVD table to determine an optimal ILVD value under a specific patient condition when MSP mode is selected. In another example, the stimulation control circuit 230 may refer to AVD table to determine an optimal AVD under a specific patient condition irrespective of pacing site or pacing mode.

Figure 6:
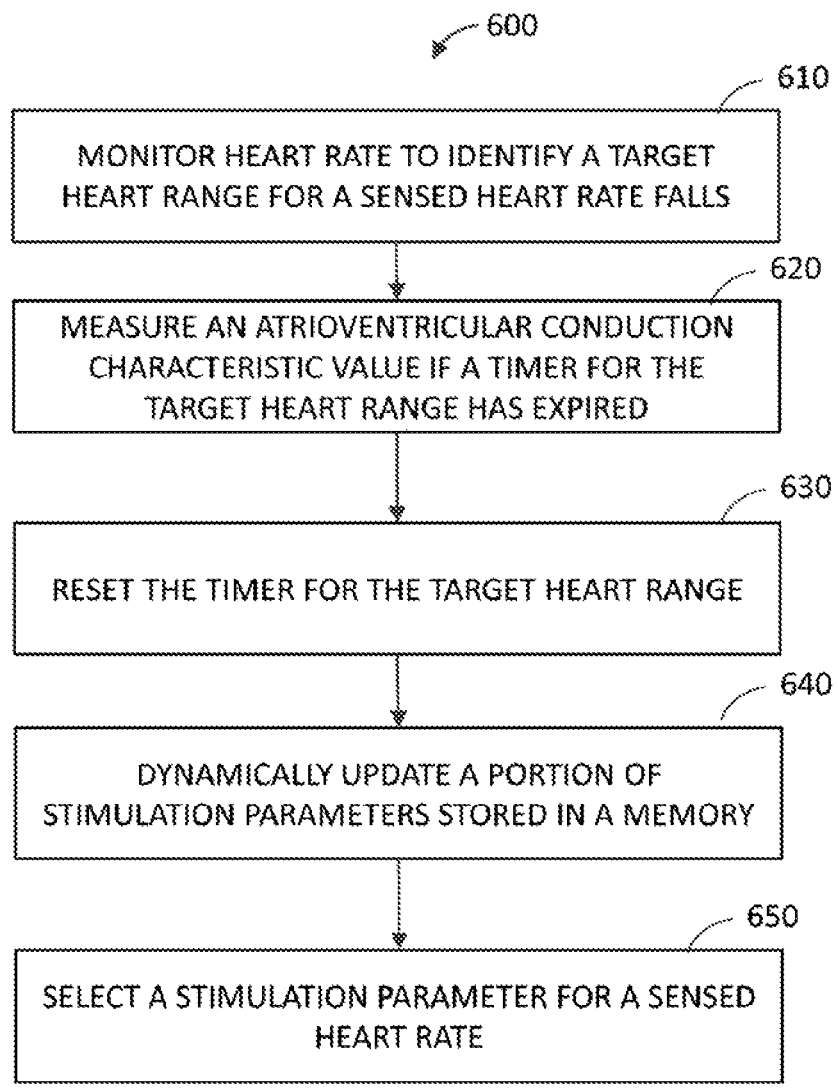
FIG. 6 is a flow chart illustrating a method for updating a stimulation parameter and delivering cardiac stimulation using the updated stimulation parameter.

FIG. 6 is a flow chart illustrating a method 600 for updating a stimulation parameter and delivering cardiac stimulation using the updated stimulation parameter. The stimulation parameter, such as a stimulation timing parameter, may be updated using intrinsic AV conduction characteristics (e.g., AVI) that are sampled by a plurality of timers corresponding to a plurality of heart rate ranges. The method 600 can be implemented in and executed by an implant device, such as the IMD 110, or the dynamically controlled cardiac stimulation system 200.

The method 600 commences at 610, where patient heart rates can be monitored continuously or intermittently, such as using a cardiac electrical or mechanical signal received by the sensor circuit 210. The heart rates can be intrinsic heart rates in the absence of atrial pacing. Alternatively, the heart rates can be detected during atrial pacing. Such atrial-paced heart rates are substantially equivalent to atrial pacing rates. A heart rate can be detected in a target heart rage (e.g., HR_k) among a plurality of heart rate ranges HR_1 through HR_N. The plurality of heart ranges can be non-overlapping to each other.

A set of timers Timer_1 through Timer_N can be used for timing control of sampling AV conduction characteristic. The sampling of an AV conduction characteristic refers to measuring the AV conduction characteristic (e.g., AVI) according to a schedule, such as at a particular time or a periodic sampling rate (e.g., performing a measurement once every 5 minutes). The set of timers correspond to the plurality of heart rate ranges, as illustrated in FIG. 3 in a non-limiting example. The timers can be programmed with respective timer durations, and operate independently with respective reset and expiration time. The timers can enable or disable measurement of AV conduction characteristic for the corresponding heart rate ranges based on the states of the respective timer (e.g., whether or not the timer has timed out or expired).

At 620, when the sensed heart rate is detected in the target heart rate range HR_k, if the corresponding timer Timer_k is in a timeout or expired state, then an AV conduction characteristic (e.g., AVI) value can be sampled. Upon completion of the sampling process, at 630 the Timer_k, corresponding to the target heart range HR_k, can be reset to its duration Dur_k. Timer_k then counts down as its duration Dur_k elapses, and subsequent AVI measurement is disabled for any sensed heart rate falling in the range HR_k, until the Timer_k expires.

In some examples, an AVI measurement carried out by any sampler may trigger a global blanking period ($T_B$). In an example, the global blanking period $T_B$ can be approximately 1 minute. During the global blanking period, AVI measurement in all HR ranges can be disabled, regardless of the sensed heart rate or the state of any timer (whether or not timed out).

At 640, at least a portion of a set of stimulation parameters stored in a memory and corresponding to the target heart rate range HR_k can be dynamically updated using the measured AV conduction characteristic. A stimulation timing parameter may be updated using patient physiological or functional information, such as measurements of AV conduction characteristic. The stimulation timing parameter defines the timing sequence for delivering cardiac stimulation, and can be important to ensure therapy efficacy and patient hemodynamic response. The timing parameter may include AVD, VVD, or ILVD. In an example, the AVD can be updated using patient intrinsic AVI measured at 620. In an example, the AVD can be updated recursively using a weighted combination of (1) a historical stimulation timing parameter value and (2) the determined value of the AV conduction characteristic, each scaled by respective weight factors, such as according to Equation (1) above. In an example, one or more of the weight factors may be determined using information of physical activity of the patient. For example, in response to elevated physical activity, the weight factor for historical AVD value to can be reduced and/or the weight factor for present AVI measurement can be increased, such that the updated AVD is more sensitive to the present AVI. In another example, the AVD may be updated using a combination of an AVI measured at the right ventricle ($AV_R$) and an AVI measured at the left ventricle ($AV_L$).

The updated portion of the set of stimulation parameters can be stored in the memory. The stimulation timing parameters may correspond to each of a plurality of heart rates or heart rate ranges. In some examples, the stimulation timing parameters may further correspond to other patient conditions such as atrial sensed (AS) events or atrial paced (AP) events, different postures, or different time of a day. In some examples, a stimulation parameter table may be created and stored in the memory. The table can include stimulation timing parameter values and the corresponding plurality of heart rates or heart rate ranges, optionally with one or more other patient conditions (e.g., postures), or information of time of a day, as illustrated in FIG. 5A-5C.

At 650, a stimulation parameter can be selected from the set of the stimulation parameters stored in the memory, including the updated stimulating timing parameters, for use during cardiac stimulation. For a received patient condition (e.g., a heart rate sensed from the patient, an AS or AP event, a posture, or a time of a day), a recommended stimulation parameter (e.g., AVD) corresponding to that patient condition may be identified. Cardiac stimulation (e.g., CRT) may be delivered using the selected stimulation parameter. In various examples, a heart chamber (e.g., LV-only pacing, or BiV pacing of both left and right ventricles), or a pacing mode for pacing a heart chamber (e.g., a single site pacing (SSP), or a multisite pacing (MSP), of a left ventricle), may be determined based on patient condition, as discussed above with reference to FIG. 2.

Figure 7:
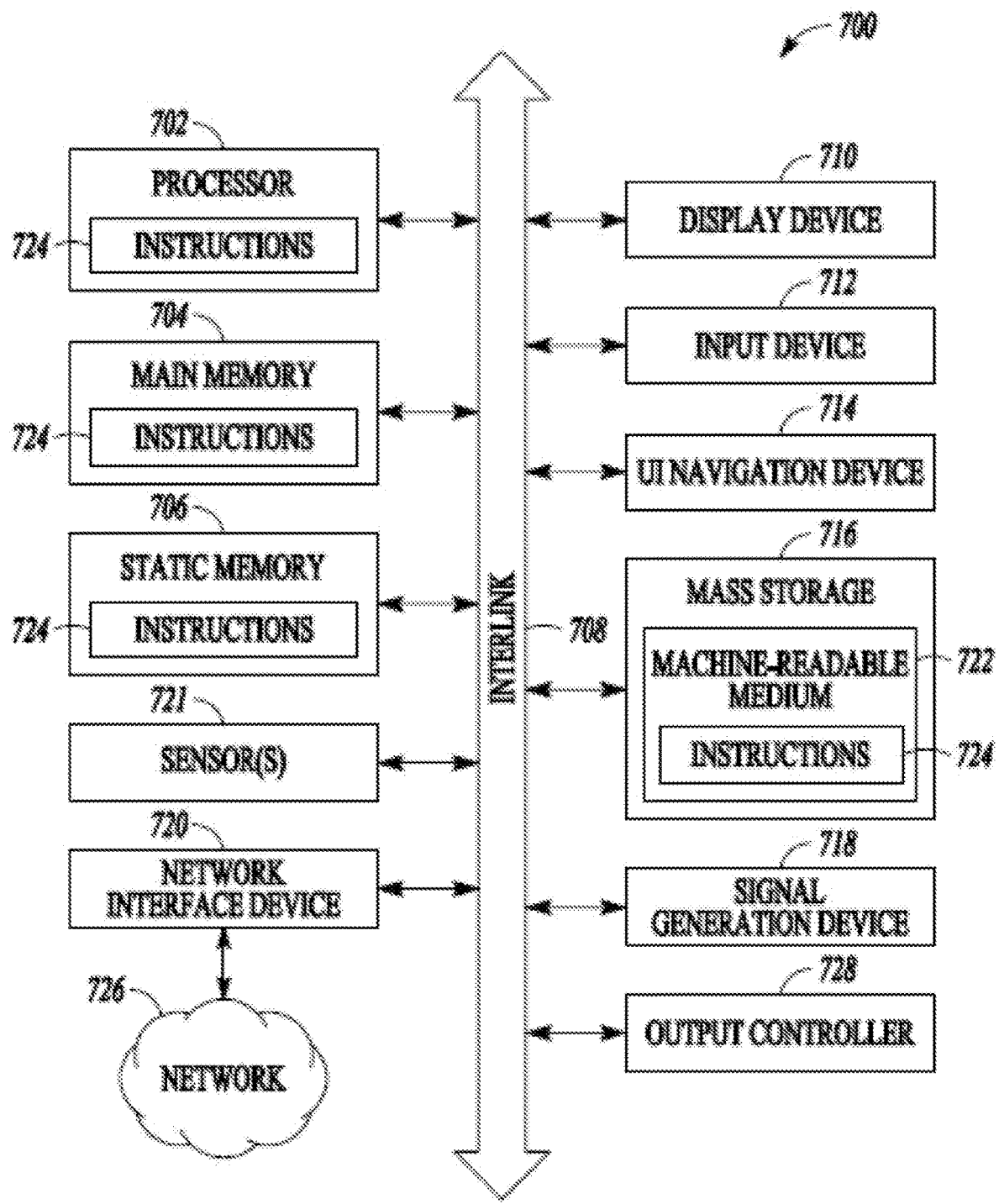
FIG. 7 illustrates a block diagram of an example machine upon which any one or more of the techniques (e.g., methodologies) discussed herein may perform.

FIG. 7 illustrates a block diagram of an example machine 700 upon which any one or more of the techniques (e.g., methodologies) discussed herein may perform. Portions of this description may apply to the computing framework of various portions of the LCP device, the IMD, or the external programmer.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A medical-device system, comprising:
   a stimulation control circuit configured to generate a control signal to deliver cardiac stimulation to a heart of a patient according to stimulation parameters stored in a memory according to a plurality of heart rate ranges, and to update at least a portion of the stored stimulation parameters, including:
   provide a plurality of timers each having a duration, wherein each of the plurality of timers corresponds to different heart rate ranges, and is configured to expire after the respective duration has elapsed from a respective reset time;
   identify, from the plurality of heart rate ranges, a target heart range in which a detected heart rate falls, and measure an atrioventricular conduction characteristic value if the timer for the target heart range has expired at the detected heart rate; and
   update at least a portion of the stimulation parameters stored in the memory and corresponding to the target heart rate range using the measured atrioventricular conduction characteristic.

2. The system of claim 1, wherein the stimulation control circuit is configured to reset the timer for the target heart rate range upon measuring the atrioventricular conduction characteristic value.

3. The system of claim 1, wherein the stimulation control circuit is configured to select a stimulation parameter value from the stimulation parameters for a detected heart rate, the system comprising a stimulator circuit configured to deliver cardiac stimulation using the selected stimulation parameter value.

4. The system of claim 1, wherein the stimulation timing parameters include atrioventricular delay (AVD) values, and the atrioventricular conduction characteristic includes intrinsic atrioventricular interval (AVI), and
   wherein the stimulation control circuit is configured to generate a control signal to suspend ventricular stimulation during the measurement of intrinsic AVI and to resume ventricular stimulation after the measurement of intrinsic AVI.

5. The system of claim 1, further comprising a global timer having a duration, and the stimulation control circuit is configured to update at least the portion of the stimulation parameters in response to an expiration of the global timer.

6. The system of claim 1, wherein the stimulation control circuit is configured to generate, in response to the measurement of an atrioventricular conduction characteristic, a control signal to disable any subsequent measurement of atrioventricular conduction characteristic during a blanking period.

7. The system of claim 1, wherein the stimulation control circuit is configured to determine a stimulation parameter for the target heart rate range using the measured atrioventricular conduction characteristic scaled a weight factor.

8. The system of claim 7, wherein the stimulation control circuit is configured to update a stimulation parameter for the target heart rate range using a weighted combination of a historical stimulation timing parameter value and the measured atrioventricular conduction characteristic each scaled by respective weight factors.

9. The system of claim 1, wherein the stimulation control circuit is configured to determine or update the respective durations of the plurality of timers using information of prevalence of heart rates detected in the corresponding plurality of heart rate ranges.

10. The system of claim 1, wherein the stimulation control circuit is configured to store in the memory a stimulation parameter table including the stimulation timing parameters and the corresponding plurality of heart rate ranges.

11. The system of claim 1, wherein the stimulation control circuit is configured to:
generate, and store in the memory, a regression model between (1) values of the atrioventricular conduction characteristic corresponding to a plurality of heart rate ranges and (2) the plurality of heart rate ranges; and
estimate a value of the atrioventricular conduction characteristic at a specific heart rate using the generated regression model.

12. The system of claim 1, wherein the stored stimulation parameters further correspond to atrial sensed (AS) events or atrial paced (AP) events at the plurality of heart rate ranges, and the stimulation control circuit is configured to select the parameter for use during cardiac stimulation using information of a AS or AP event.

13. The system of claim 1, wherein the stored stimulation parameters further include information of a pacing chamber configuration for a plurality of heart rate or heart rate ranges, the pacing chamber configuration including a left-ventricular (LV) only pacing or a bi-ventricular (BiV) pacing of both left and right ventricles,
wherein the stimulation control circuit is configured to select the LV-only pacing or the BiV pacing using an atrioventricular interval or an atrioventricular interval variability at a detected heart rate.

14. A method of operating a medical-device system to control cardiac stimulation using a plurality of timers corresponding to a plurality of heart rate ranges, each of the plurality of timers configured to expire after a respective duration has elapsed from a respective reset time, the method comprising:
monitoring patient heart rates;
identifying, from the plurality of heart rate ranges, a target heart range in which a detected heart rate falls;
measuring an atrioventricular conduction characteristic value if a timer for the target heart range has expired at the detected heart rate; and
updating at least a portion of a set stimulation parameters stored in a memory and corresponding to the target heart rate range using the measured atrioventricular conduction characteristic;
wherein the stimulation parameters include stimulation timing parameters corresponding to the plurality of heart rate ranges.

15. The method of claim 14, wherein storing the stimulation parameters includes storing in the memory a stimulation parameter table that includes the stimulation timing parameters for atrial sensed (AS) events or atrial paced (AP) events and corresponding to the plurality heart rate ranges.

16. The method of claim 14, wherein the stimulation timing parameters include atrioventricular delay (AVD) values, and the atrioventricular conduction characteristic includes intrinsic atrioventricular interval (AVI), and wherein the method comprising:
generating a control signal to suspend ventricular stimulation during the measurement of intrinsic AVI; and
after the measurement of intrinsic AVI, resuming ventricular stimulation and resetting the timer for the target heart rate range.

17. The method of claim 14, comprising, subsequent to the measurement of intrinsic AVI, generating a control signal to disable any subsequent measurement of intrinsic AVI during a blanking period.

18. The method of claim 14, comprising determining or updating the respective durations for the plurality of timers using information of prevalence of heart rates detected in the corresponding plurality of heart rate ranges.

19. The method of claim 14, wherein updating at least a portion of the stimulation parameters includes using a weighted combination of a historical stimulation timing parameter value and the measured atrioventricular conduction characteristic each scaled by respective weight factors.

20. The method of claim 14, further comprising selecting a stimulation parameter value from the stimulation parameters for a detected heart rate, and delivering cardiac stimulation via a stimulator circuit using the selected stimulation parameter value.

* * * * *